United States Patent
Lopez-Goerne

(10) Patent No.: US 8,343,514 B2
(45) Date of Patent: Jan. 1, 2013

(54) SOL-GEL NANOSTRUCTURED TITANIA RESERVOIRS FOR USE IN THE CONTROLLED RELEASE OF DRUGS IN THE CENTRAL NERVOUS SYSTEM AND METHOD OF SYNTHESIS

(75) Inventor: Tessy Maria Lopez-Goerne, Deleg. Tlalpan (MX)

(73) Assignee: Universidad Autonome Metropolitana, Tlalpan (MX)

(*) Notice: Subject to any disclaimer, the term of this patent is extended or adjusted under 35 U.S.C. 154(b) by 611 days.

(21) Appl. No.: 12/303,953

(22) PCT Filed: Jun. 6, 2006

(86) PCT No.: PCT/IB2006/001725
§ 371 (c)(1),
(2), (4) Date: Aug. 12, 2009

(87) PCT Pub. No.: WO2007/141590
PCT Pub. Date: Dec. 13, 2007

(65) Prior Publication Data
US 2010/0233230 A1 Sep. 16, 2010

(51) Int. Cl.
*A61K 9/00* (2006.01)
*A61F 13/00* (2006.01)
*C22C 14/00* (2006.01)
*C22C 29/00* (2006.01)
(52) U.S. Cl. ......... 424/400; 424/422; 420/417; 420/578
(58) Field of Classification Search .................. None
See application file for complete search history.

(56) References Cited

U.S. PATENT DOCUMENTS

| | | | |
|---|---|---|---|
| 6,117,814 A | 9/2000 | Plecha et al. | |
| 2004/0121451 A1* | 6/2004 | Moritz et al. | 435/287.2 |

FOREIGN PATENT DOCUMENTS

| | | |
|---|---|---|
| EP | 1016637 A | 7/2000 |
| WO | 9603117 A | 2/1996 |
| WO | 0162232 A | 8/2001 |
| WO | 2005089825 A | 9/2005 |

OTHER PUBLICATIONS

Hutter, R. et al., Epoxidation of beta-isophorone over a Titania-Silica Aerogel: Effect of Catalyst Pretreatments with Bases, Journal of Cataysis 172, 427-435 (1997).*
Ebadi, M., et al., Therapeutic efficacy of selegiline in neurodegenerative disorders and neurological diseases, Curr Drug Targets (Nov. 2006) 7(11) pp. 1513-1529 (abstract).*

* cited by examiner

*Primary Examiner* — Brian-Yong S Kwon
*Assistant Examiner* — Lyndsey Beckhardt
(74) *Attorney, Agent, or Firm* — Browdy and Neimark, P.L.L.C.

(57) ABSTRACT

The invention is related to a sol-gel nanostructured titania reservoir and its synthesis which is biocompatible with brain tissue. The pore size distribution, crystallite size and the extent of the crystalline phase distribution of anatase, brookite and rutile can be fully controlled. This device may be used to contain neurological drugs. It may be inserted directly into brain tissue for the purpose of the controlled time release of drugs over a period of from 6 months to three years.

7 Claims, 9 Drawing Sheets

Figure 1:
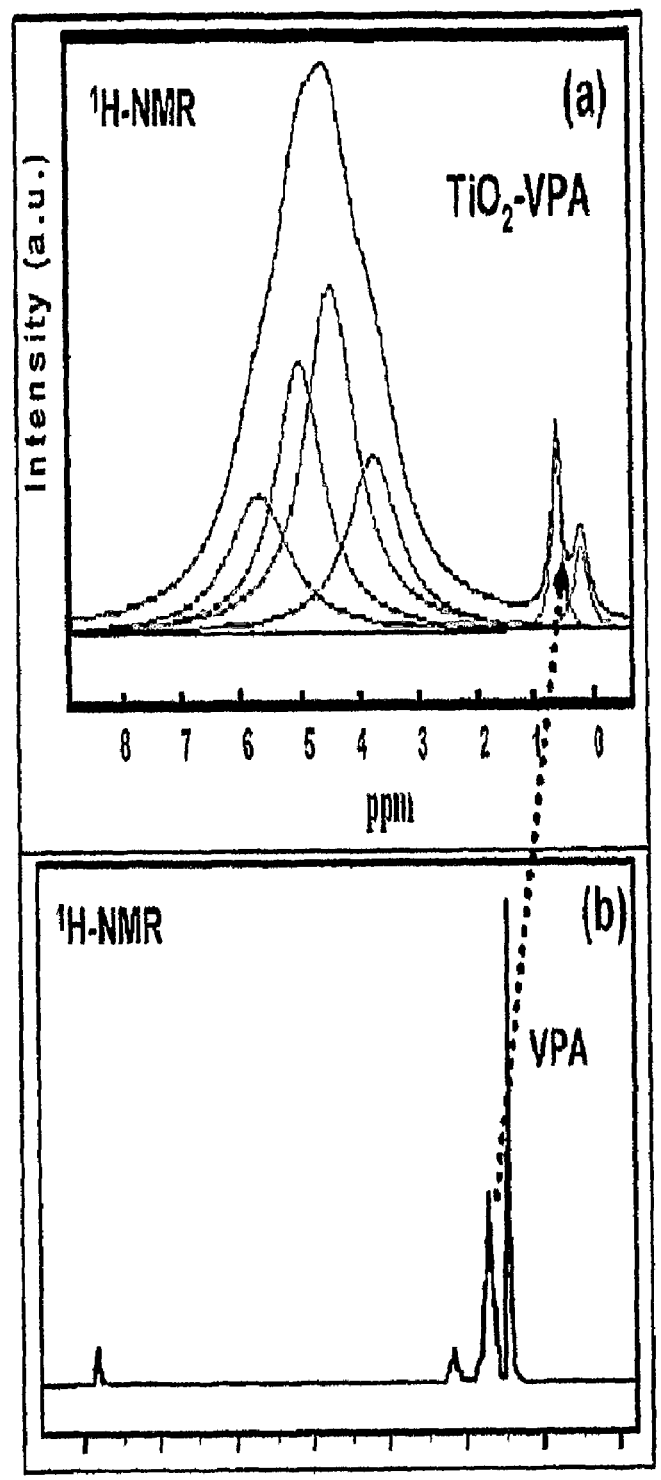

SOL-GEL NANOSTRUCTURED TITANIA RESERVOIRS FOR USE IN THE CONTROLLED RELEASE OF DRUGS IN THE CENTRAL NERVOUS SYSTEM AND METHOD OF SYNTHESIS

FIELD OF THE INVENTION

This invention is related to the synthesis of a titania reservoir which is biocompatible with brain tissue. The pore size distribution, crystallite size and the extent of the crystalline phase distribution of anatase, brookite and rutile can be fully controlled. This device will be used to contain neurological drugs. It will be inserted directly into brain tissue for the purpose of the controlled time release of drugs over a period of from 6 months to three years.

BACKGROUND FOR THE INVENTION

State of the art research in the treatment of chronic diseases is based on the development of controlled release systems capable of delivering drugs rapidly and efficiently to where they are needed. A major requirement is that these devices should insure delivery and penetration of the drug to the active site. New nanostructured materials represent an efficient way to administer medications and biological products in future applications[1-5]. Hydrogels based on N-isopropylacrilimide and metacrilic acids (MAA) have recently received considerable attention. This is due to their ability to swell in response to the stimulation of the medium[6-8]. In the solid state, the existence of interpolymeric complexes in which monomers are linked together through hydrogen bonds has been observed. These linkages occur under acid conditions and are stabilized through hydrophobic interactions. This leads to a marked dependence on the pH of the medium in which swelling occurs. This swelling is also strongly dependent on the degree of cross-linking. The use of drug delivery by oral means has received considerable attention, particularly in cases in which activation is controlled by variations in the pH. Copolymers having a high concentration of N-isopropylacrilamide appear to be the most effective in enabling one to obtain different cut-off curves used in the drug model.[12-15]

In the majority of cases, which involve controlled drug release, the medication or other biological agent, is introduced into the interior of the reservoir normally known as the transporter. The transporter usually consists of a polymeric material. Under normal conditions the rate of drug release is controlled by the properties of the polymeric material which constitutes the transporter. However, other factors may also be rate determining. When these factors are taken into account, it may be possible to insure a slow, constant rate of drug delivery over extended periods of time.[16-18] The use of these materials has lead to considerable advances in drug delivery when compared to systems currently in use. In conventional drug delivery systems, drug concentrations reach a maximum value only to decay, finally reaching a concentration, which requires the administration of another dose. Additionally, if the maximum drug concentration exceeds the safe level or if, alternatively it falls below the required dose, cyclic periods will occur during which the drug is not producing the desired effect. This is generally known as "variations in tisular exposure". When controlled drug release is used, it may be possible to maintain drug concentrations, which fall between the maximum allowed rate, and the minimum concentration at which the rate is effective[19-21].

In order for the drug to be delivered to the desired site, diffusion from the surface of the transporter to the medium surrounding the transporter must occur. From this point, the drug must diffuse over an area in which it will be effective. Following many studies, it has been concluded that there are four general mechanisms by which controlled drug release can be classified: 1) diffusion controlled systems, 2) chemically controlled systems, 3) systems activated by a desolubilizer and, 4) systems which are magnetically controlled.

The migration of a drug to a fluid medium for a system such as that described here, must involve a process in which the drug is desorbed from the surface of the transporter and is simultaneously absorbed into the fluid medium. This process is controlled by a concentration gradient. The fluid might consist of either water or a biological fluid. The entrance of a solvent into a polymer, which is in a vitreous state, may produce a considerable increase in the macromolecular motion. From a thermodynamic point of view, a solubility parameter d, and the interaction between the material and the solvent c, can express the compatibility between the solvent and the reservoir. If the solid is only slightly compatible with the polymer, it will remain in the vitreous state and under these conditions the controlled release of any drug will be very slow and of limited pharmacological use. On the other hand if the thermodynamics are favorable, the probability that the solute can diffuse from the transporter to the fluid is very large (Korsmeyer and Pepas, 1984 and Lee 1985a).[22] In 1971 Yasuda and Lamaze refined their theory on free volume and noted that they could predict the diffusion coefficient of a drug across a polymeric matrix with considerable accuracy[23]. In this treatment they showed that the normalized diffusion coefficient of the solute in the polymer and the diffusion coefficient of the solute in the pure solvent are related by the extent of hydration. The external transport of the drug is caused by the dissolution of the solute at the interface between the solute and the reservoir followed by external diffusion under the influence of a concentration gradient, which obeys Fick's first law (Langer and Peppas, 1983)[24]. These systems are capable of drug release at a constant rate. However, in practice factors exist which may lead to large deviations. This problem can usually be corrected by adjusting or changing the geometry of the device. When the system is a monolith, the active compound is uniformly distributed on the support of the solid polymer.

The drug may be dissolved within the polymer matrix or dispersed depending on whether its concentration is such that its solubility in the polymer has been exceeded. The migration of the drug to the fluid medium occurs as a result of molecular surface diffusion along the support or by pore diffusion through the micro and meso pores within the matrix of the polymer. In this case, diffusion can be interpreted using Fick's second law. However, in any case the migration of the drug to the fluid medium will decrease as a function of time. This decrease occurs as a result of an increase in the length of the diffusion path[25] (Rhine et.al., 1980).

The drug is chemically bound to the polymer chain and is released as a result of a hydrolytic cleavage. The rate of drug release can be altered if the hydrolysis can be catalyzed by enzymes (Kopeck et. al, 1981)[26]. Other systems of continual drug release include polymers formed from polylactic acid and its copolymers[30]. These precursors, together with glycolic acid have been used primarily due to their biodegradability and biocompatibility. The microencapsulation of drugs[31-32] from a technical point of view can be defined as a process, which involves the covering of drugs. This may occur as molecules, solid particles or liquid globules. The materials used in the encapsulation process will depend on the particular application. However, the process will give rise to particles having micrometric dimensions. The products, which are formed as a result of this process, are referred to as "microparticles", microcapsules' or "microspheres".

These systems differ in their morphology and internal structure. However, they are all similar in size which is approximately 1 mm[33-34]. When the particle size is less than 1 μm, the resultant products of the microencapsulation process are referred to as "nanospheres", "nanoparticles" or nanocapsules"[35-37]. An important feature of the microencapsulation process is that the products are not limited to drugs or biological materials but are extended to include products in such areas as agriculture, cosmetics and food[38].

There are other areas in which controlled drug delivery is used. These include medications, which are absorbed through the skin. Creams and gels, which can be applied to the skin, have been used for many years as sedatives and medications to eradicate localized infections. They can also be used to treat the entire body (systemic)[39]. An increasing number of medications have recently become available as transdermal patches. They adhere to the skin through an adhesive ring while a thin film of the medication[40] covers the center of the patch. The medication is slowly absorbed through the skin until it is absorbed into the blood stream. The transdermal patches most frequently used include testosterone, estrogens, sedatives, birth control and nicotine patches (used to aid smoking cessation). Other patches such gabapentin deliver anticonvulsant medications (Neurontin)[41-43]. In some cases, the active medication is mixed with another substance that controls the rate at which it is absorbed. This means that they can be used continually for longer periods of time or even for several days.

Another method by which transdermic administration is applied makes use of small receptacles, which use air pressure to inject a small stream of medication through the upper layers of skin. People who require insulin on a daily basis can make use of some very small receptacles to administer the medication[44]. Researchers involved in gene therapy to treat HIV have experimented with this technology to inject genetic materials through the skin or muscle tissue[45-46]. Medications can also be delivered through mucous membranes. A large number of the drugs are administered through the lungs or through the nasal passage and are rapidly absorbed into the blood stream. A large gamut of medications, including painkillers and vaccinations can be applied using this technique. In what promises to be a significant advance in the treatment of diabetes, a new technique, which makes use of inhalation technology, is being tested. Patches can also be adhered in the mouth at the interior of the cheek muscles[47-50].

In order to avoid the formation of a spinel, the sol-gel technique can be used as a good method by which the various solid phases can be controlled (T. Lopez et.al., Catalysis Today 35, 293, 1997). A greater degree of control can be achieved in comparison to other methods of synthesis. One can tailor make the reservoir to fit specific applications by using this method. Advances include:
(i) Superior homogeneity and purity
(ii) High biocompatibility with brain tissue
(iii) Better nano and microstructural control of the polymeric reservoir.
(iv) Greater BET surface area.
(v) Improved thermal stability of the drugs attached to the reservoir.
(vi) Well-defined pore size distributions.
(vii) The ease by which drugs can be attached and released from the reservoir.
(viii) Inorganic chain structures can be generated in solution
(ix) A finer degree of control over the hydroxylation of the reservoir can be achieved.

The process of reservoir fabrication has as an objective the optimization of the following variables: particle size, mean pore size, interaction forces and the degree of functionalization. It may also be desirable to modify the textural and electronic behavior of the reservoir.

Titania is a material, which has important applications in industry. As an example we cite the synthesis of hydrocarbons from carbon monoxide or synthesis gas (U.S. Pat. No. 4,992, 406; U.S. Pat. No. 4,794,099; U.S. Pat. No. 5,140,050; U.S. Pat. No. 521,553; U.S. Pat. No. 6,124,367.

Due to its unique electronic properties it has been used to modify the electronic properties of a transition metal when it is used as a reservoir (Klein L. C., Sol-Gel Technology for Thin Films, Fibers, Perform, Electronics and Shapes, (Noyes: New: New Jersey 1997)

Under conditions of normal atmospheric pressure, titania can have three different crystal phases: brookite, anatase and rutile. In all three phases, the Ti atoms are centered inside deformed oxygen octahedra. The number of edges of these octahedra that are shared distinguishes the different crystalline phases. Three octahedral edges are shared in brookite, four in anatase, and two in rutile (L. Pauling, JACS 51 (1929) 1010. This results in a different mass density for each phase. Pure titania with a large crystallite size is stoichiometric, dielectric and not useful in catalysis. It is necessary to change the stoichiometry by creating oxygen vacancies or other bulk defects.

The electronic and catalytic properties of titania depend on the local density and on the type of impurities present in the crystal structure (R. H. Clark "The chemistry of Titanium and Vanadium, Elsevier Publishers Co. N.Y. 1968, Ch 9).

Sol-gel technology is an important synthesis method by which the crystalline phases and particle size of titania can be controlled. A sol is a fluid, colloidal dispersion of solid particles in a liquid phase where the particles are sufficiently small to stay suspended in Brownian motion. A "gel" is a solid consisting of at least two phases wherein a solid phase forms a network that entraps and immobilizes a liquid phase.

In the sol-gel process the dissolved or "solution" precursors can include metal alkoxides, alcohol, water, acid or basic promoters and on occasion salt solutions. Metal alkoxides are commonly employed as high purity solution precursors. When they react with water through a series of hydrolysis and condensation reactions they yield amorphous metal oxides or oxyhydroxide gels. When the volatile alcohol's are removed the result is the formation of crystalline solid compounds.

The materials that are used as colloid precursors can be metals, metal oxides, metal oxo-hydroxides or other insoluble compounds. The degree of aggregation or flocculation in the colloidal precursor can be adjusted in such a way that the pore size distribution can be controlled. Dehydration, gelation, chemical cross-linking and freezing can be used to form the shape and appearance of the final product. Some advantages using sol-gel technology include control over the purity of the alkoxide precursors, control over the homogeneity of the product, control over the evolution of the desired crystalline phases and most importantly, the reproducibility of the materials synthesized.

For $H_2O/Ti(OR)_4$ ratios of between 0 and 0.1, the titanium alkoxide reacts immediately with water and alcohol. During the hydrolysis, the hexacoordination of the central titanium remains (T. Boyd, J. Polymer Sci., 7(1951)591). The hydrolysis product is not fully hydrolyzed nor can it ever be a pure oxide. It can only be in the form, $$Ti_nO_{2n-(x+y)/2}(OH)_x(OR)_y$$

Where n is the number of titanium atoms polymerized in the polymer molecule and x and y is the number of terminal OH and OR groups respectively. It is well known that some sol-gel structures attain their highest coordination state through intermolecular links (Sankar G., Vasureman S, and Rao C. N. R., J. Phys. Chem, 94, 1879 (1988)). Because there are strong Van der Wall interaction forces between the drugs and the titania reservoir, it is possible to encapsulate a large amount of medication within the titania reservoir.

Additional Titania Patents using Sol-Methods

U.S. Pat. No. 6,124,367. This patent protects reservoirs used in the Fischer Tropsch reactions from sintering by imparting a higher degree of mechanical strength to the reservoir. It incorporates $SiO_2$ and $Al_2O_3$ into the reservoir and claims a rutile—anatase ratio of 1/9. It is a porous reservoir with either a spherical or a cylindrical shape. It is made by extrusion, spray drying or tableting.

U.S. Pat. No. 6,117,814. This patent describes a titania reservoir which also incorporates silica and alumina as a binder into the structure. The purpose of the binder is to impart better mechanical properties to the reservoir. The size range of this reservoir is from between 20 to 120 microns. The reservoir is approximately 50% binder, which is fabricated by a sol-gel process.

U.S. Pat. No. 6,087,405. This patent describes a reservoir to be used in a Fischer Tropsch gas synthesis reaction. The reservoir incorporates group VII metals into its structure. The rutile-anatase ratio in the structure is a distinguishing feature of this patent.

OBJECTIVES

1. The development of nanostructured materials for use in the time controlled release of drugs in the central nervous system (CNS)

2. Optimization of materials to enable control of the following parameters: pore size distribution, particle size, crystalline phase, degree of functionalization, size of reservoir required to accommodate the drug, and release time for effective delivery 3. Obtain constant drug delivery times to damaged neurons and to prevent an overdose to the blood stream, liver, intestine and to the hematoencefalic barrier.

4. Construct complex systems, which mimic the central nervous system in order to obtain specific diffusion and kinetic delivery rates.

5. Due to the nature of the products it is essential to coordinate preparation times with administration time to patients. If this is not correctly assessed, drug delivery concentrations may not be correct. Drug retention times in the reservoirs must be carefully studied.

6. It will be important that a constant rate of drug release be maintained for periods of between six months and three years.

7. The reservoirs will consist of nanostructured titania prepared using sol-gel methods.

DETAIL OF THE INVENTION

The present invention includes a novel nano-material (silica, titania and silica-titania) obtained by the sol-gel process. Neurological drugs having an active molecular size of between 1.5 to 4.0 nm can be occluded within the interior of this device.

This nano-material consists of partially hydrolyzed nano-materials having a Ti:Si range of compositions between (100:0 and 0:100). These materials were prepared using a sol-gel process, which has been used to synthesize ceramic and glass materials.

During the drying operation, the temperature was controlled in order to stabilize the internal stresses and bonds within the gel. If the material is not given sufficient time to relax, under controlled vacuum and temperature conditions in the rotavapor, significant cracking and break-up of the material may occur.

Following the drying process the hydroxyl groups remain stable within the matrix. Polymerization continues for a considerable period of time following gelation. This is referred to as the aging process, which results in a much more stable gel.

The titania, silica and titania-silica xerogels (100:0, 0:100) materials are found to be biocompatible with surrounding tissue.

In a prior article, the slow time release of drugs into the brain from an implanted device has been described in terms of months. Release times well in excess of a one-year period are needed.

The rate of drug release from an implanted device is strongly dependent on the strength of the drug-device interaction. For weak interactions the release time may be too fast. If the interaction is very strong the drug release time may be too slow.

The electronic structure of the device is controlled to obtain the adequate release of the neurological drug.

The rate of drug release is described in a previous study. If the drug is basic an acidic device is preferable. On the other hand, when the released drug is acidic a basic device should be used. Drug dispersions within the matrix are between 90 and 100%. The time release profiles in addition to being dependent on drug-device interactions, are also dependent on pore diffusion and consequently, on the porosity of the gel.

When the synthesis of the pure $TiO_2$ device was performed under acid conditions at a pH=2, the BET surface area of the device was relatively constant at approximately 500 $m^2/g$ and was found to be independent of the amount of neurological drug (i.e. anticonvulsant drug) adsorbed. When the loading of the drug approached 1000 mcg/20 g of the device, there was a slight decrease in the surface area.

When the synthesis of the device was performed under basic conditions at pH=12 the BET surface area was relatively constant at approximately 680 $m^2/g$. It was found to be independent of the loading of neurological drug (i.e. an anticonvulsant drug), for all drug loadings up to an including 1000 mcg/20 g of the device. The results described under 9 and 10 show the remarkable flexibility of the device. When synthesis is performed under acid conditions basic drugs are weakly bound to the device.

Pore volumes and pore diameters are not strongly affected by drug loadings. However, there is a small decrease in both pore volume and pore diameter at very low drug loadings.

The kinetics of the drug release process show a zero order dependence on the concentration of the encapsulated drug The zero order kinetics of the drug release delivery process ensures a constant rate of delivery.

Drug-device interactions occur through Van der Waals forces and hydrogen bonding between hydroxyl groups on the device and carbonyl groups on the drug.

The diffusion is controlled by two phenomena: a) a chemical interaction between the device and the drug, and b) mean pore size.

Following the depletion of the neurological medication, a fresh dose of the drug may be easily replaced using stereotaxic surgery.

Drug delivery using devices prepared using Sol-gel chemistry are currently state of the art. The porosity of the nano-material can be controlled by the pH of the solution. On the other hand an acid catalyst is not needed when the drug is acidic. Drug dispersions in the matrix are between 90 to 100%.

The drugs can be encapsulated during the gelling process. It can be seen from the release profiles that the drug release is based on the porosity of the gel.

The ceramic material in this invention is completely biocompatible with the brain tissue surrounding the implant.

Detailed Description of the Synthesis Methods Used

Sol-gel $TiO_2$, $TiO_2$-silica and $SiO_2$ or (sol-gel $TiO_2$—$SiO_2$ 0:100 to 100:0). In the three-necked flask shown in the figure, a mixture consisting from 36 ml of dionized water, 0 to 50 ml of (EDTA) ethylene diamine tetraacetic acid and 190 ml of ter-butanol (Baker, purity 99%) were refluxed. Prior to initiating the reflux, the pH of the solution was adjusted to 2 using $HNO_3$ in one case and 12 using ammonium hydroxide in another case. In either case, the acid or base was added in a dropwise manner until the desired pH was reached. The pH was continually monitored by means of a potentiometer throughout the entire process. Using two funnels, 87 ml of titanium n-butoxide (Aldrich, 98% purity) and 21.5 ml of tetraethoxysilane were added to the solution being refluxed. The dropwise addition was performed over a four-hour period in order to enhance the nucleation and the functionalization of the hydroxyl (OH) and the ammonium groups (NH). Following the addition of the alkoxides, the colloidal suspension was refluxed for an additional period of 24 hours. Following this process, the samples were dried under vacuum conditions in a roto-vapor ($10^{-3}$ mm. Hg) in order to remove excess water and alcohol. Finally, the samples were dried at 30° C. for 72 hours. In order to reach the final drying temperature of 30° C., the temperature was increased at a rate of 0.25° C./min) using a conventional inert atmosphere furnace.

The Effect of Synthesis Variables on the Physical Properties of the Products Obtained (1) The role of pH. An increase in pH from 3 to 9 results in a substantial decrease in the percentage of Brookite in the crystal structure. For example, at 300° C. the percentage of Brookite decreases from 13.6% to 0% when the pH is increased from 3 to 5, while that of Anatase increases from 84.7 to 100% over the same pH range. The percentage Rutile also decreases from 8.2 to 0% over the same pH range. The dominant structure appears to be Anatase at all pH's from 3 to 9 at 300° C. See Table 1

(2) The role of Temperature. When the calcination temperature is increased from 70 to 900° C., both Brookite and Anatase decrease drastically to 0° C. at 900° C. while Rutile becomes the dominant crystal phase. Over the same temperature range, Rutile increases from 1.7 to 100%. See Table 1.

(3) The role of pH and temperature on the average crystallite size of Brookite. The average crystallite size increases substantially with temperature between 70 and 300° C. at a pH of 3. However, when the pH is increased to 7, there is no noticeable change in the crystallite size over the same temperature range. Changes in the lattice parameters of Brookite appear to be more dependent on pH than on temperature. These results are summarized in Table 2.

(4) The role of pH and temperature on the physical properties of Anatase. These results are shown in Table 3. An increase in the calcination temperature at a given pH results in a sharp increase in crystallite size. This observation holds for all of the pH's studied. The lattice parameters are less dependent on pH and calcination temperature. Sintering appears to be considerably more noticeable at pH 3 than at higher pH's. This is apparent from the rather large increase in density between 70 and 600° C. The titanium occupancy increase with temperature at all pH's (5) The role of pH and temperature on the physical properties of Rutile. These results are shown in Table 4. An increase in crystallize size is observed with an increase in temperature. However, the effect is considerably less than that observed for Brookite and Anatase. This increase is observed at all the pH's studied with the exception of pH 5 in which a slight decrease in crystallite size was observed. The occupancy of titanium is not strongly dependent on particle size or temperature.

FIGURE CAPTIONS

FIG. 1. H NMR of: a) TiO2-VPA and b) pure valproic acid.

Figure 2:
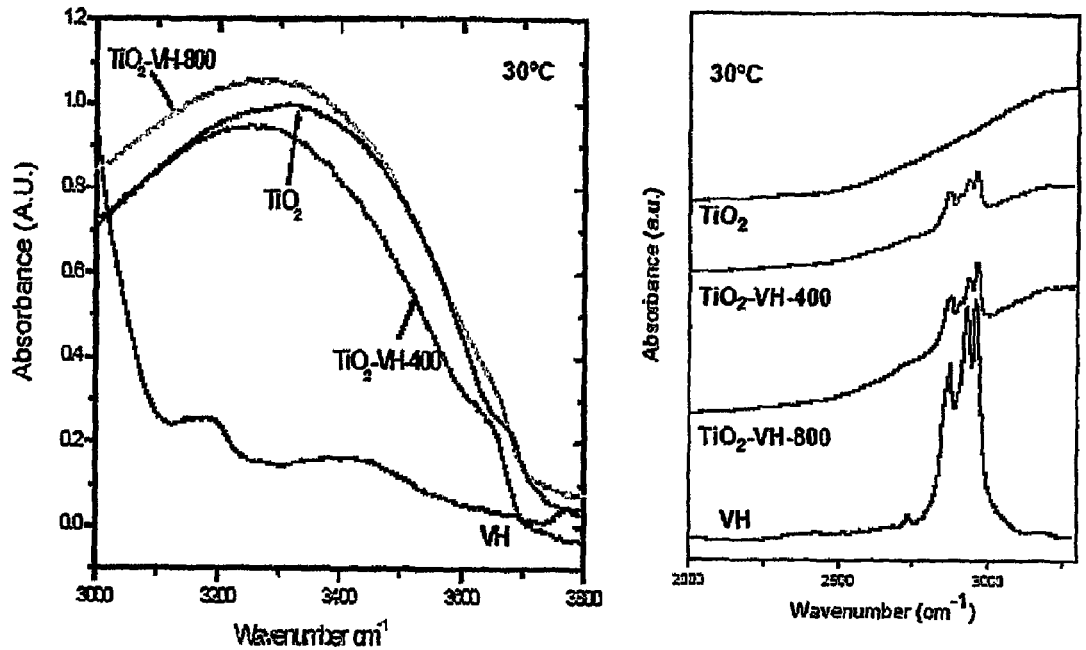

FIG. 2. FTIR spectroscopy of TiO2 and TiO2-VPA reservoir.

Figure 3:
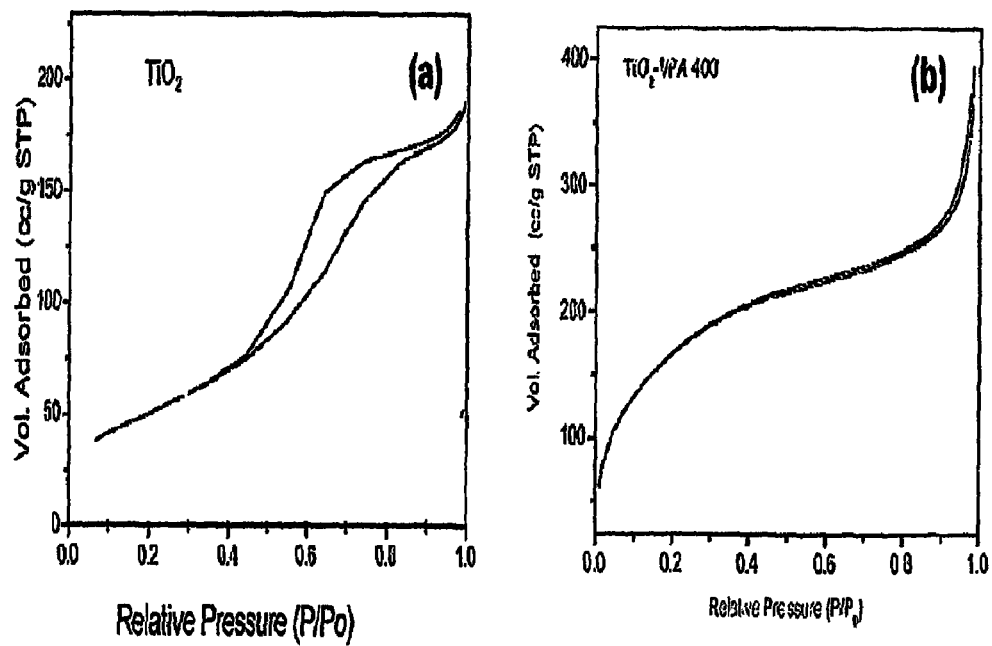

FIG. 3. N2 adsorption isotherms of empty TiO2 reservoir and TiO2 with VPA occluded.

Figure 4:
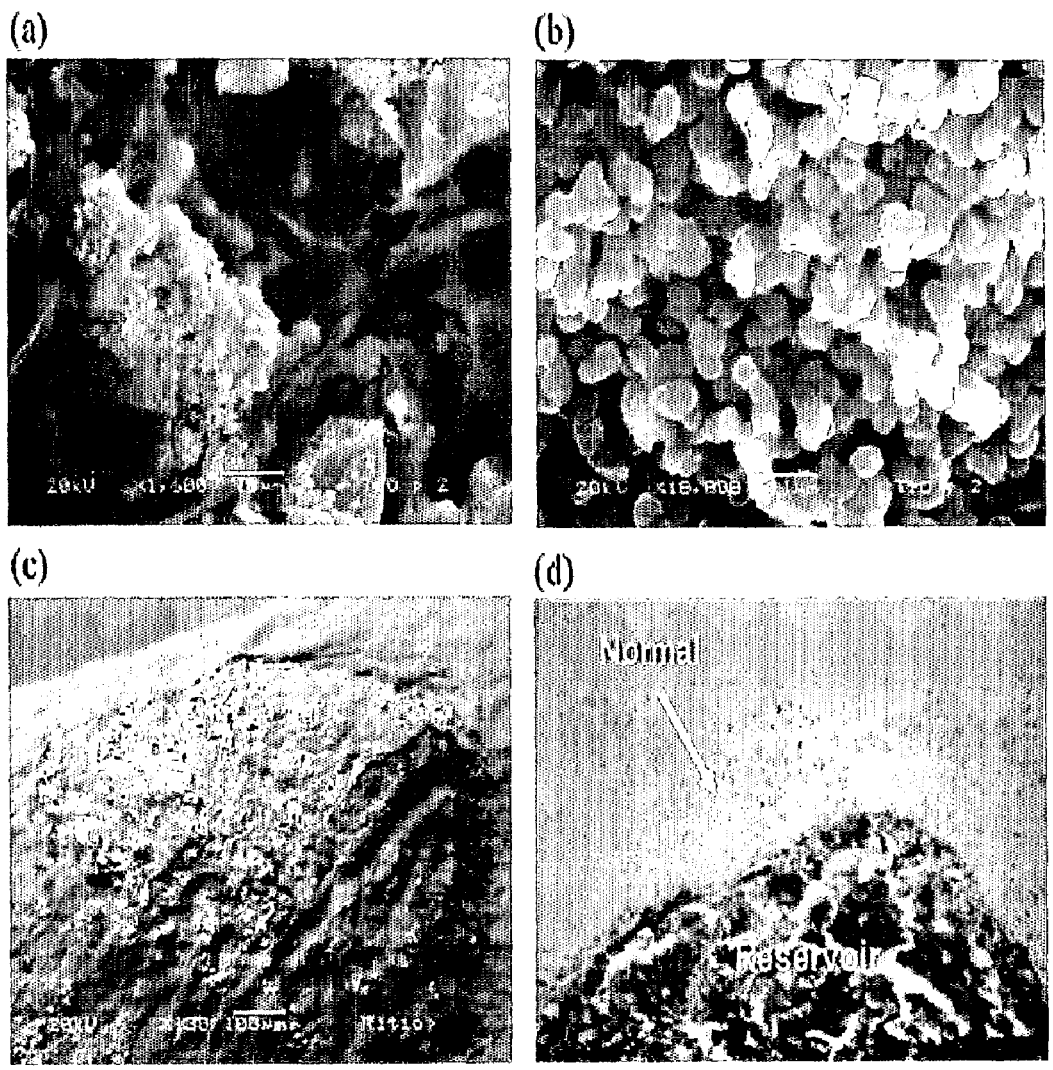

FIG. 4. Scanning Electron Microscopy (SEM) images of a TiO2 reservoir implanted in the hipocampus region: (a) Detail of the tissue mixed with the reservoir nanoparticles (b) Frontier (c) Panoramic, between hippocampus tissue and reservoir, and (d) Detail of the implanted tissue.

Figure 5:
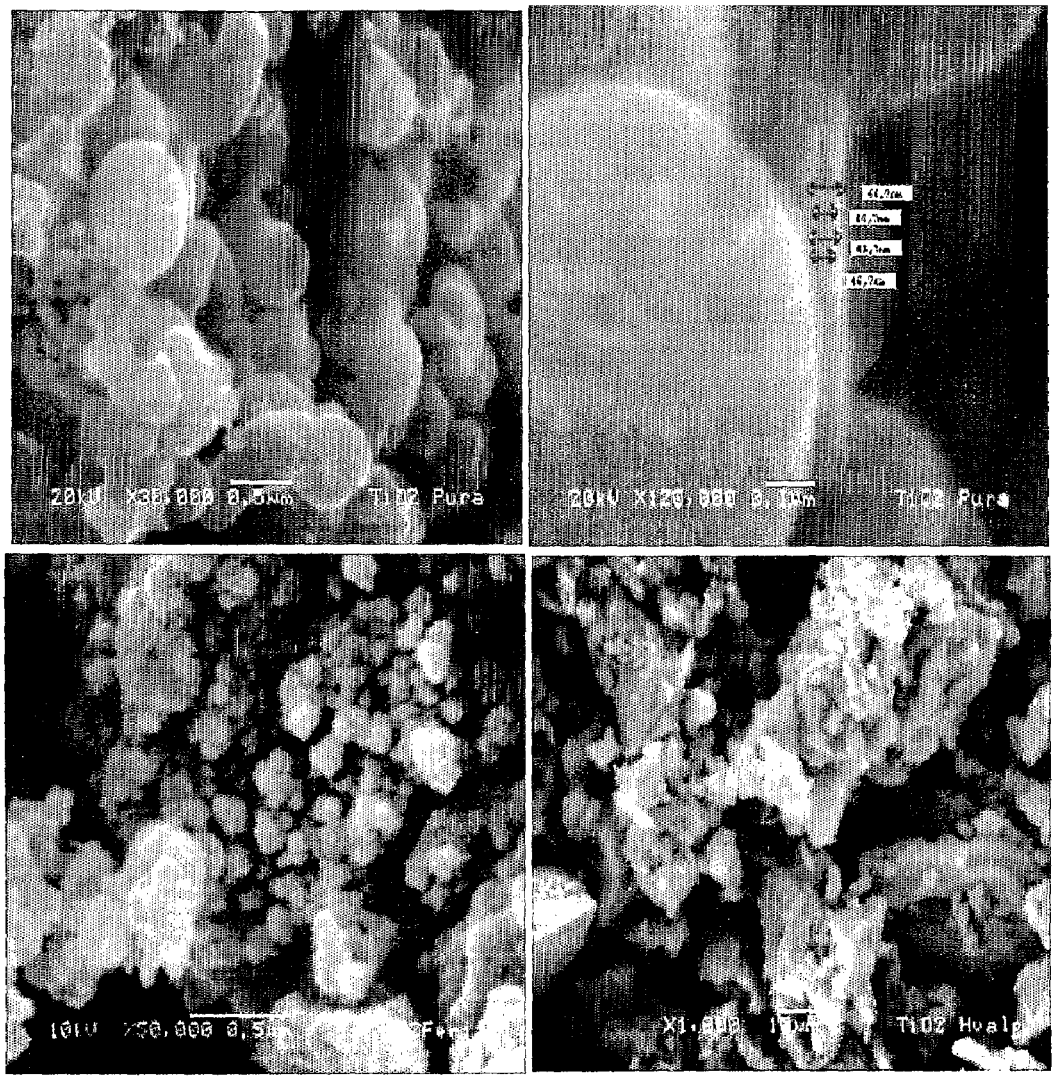

FIG. 5. Scanning Electron Microscopy (SEM) images of a sol-gel TiO2 reservoir obtained at: (a) pH7 (30,000×), (b) pH 7 (120,000×), (c) pH 9 and (d) pH 3. Note the difference in structure obtained at pH 7 and pH 3. An increase in acidity results in a change from a spherical to a more fiber like structure.

Figure 6:
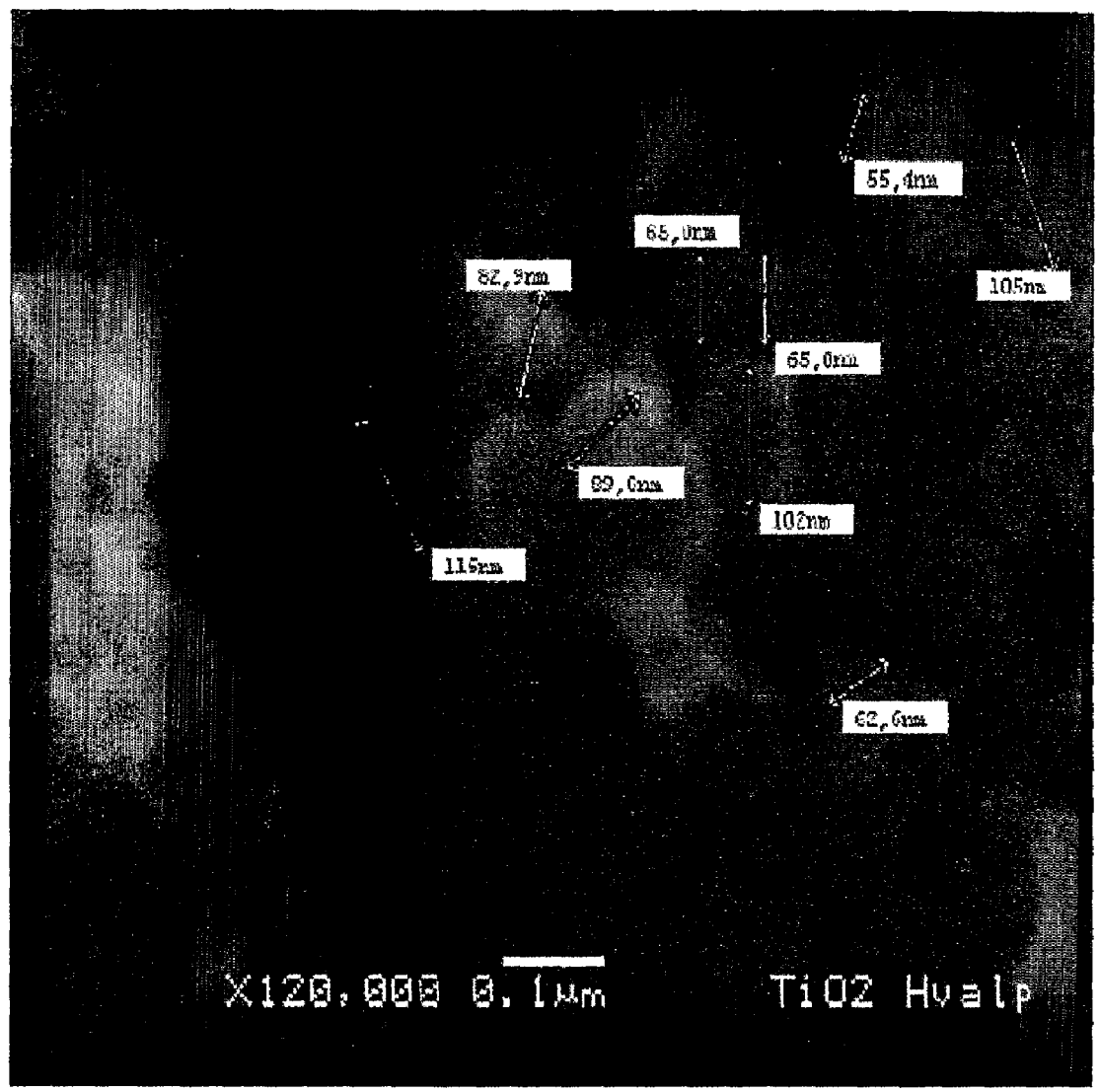

FIG. 6. Scanning Electron Microscopy (SEM) images of a sol-gel TiO2 reservoir 120000×. Detail.

Figure 7:
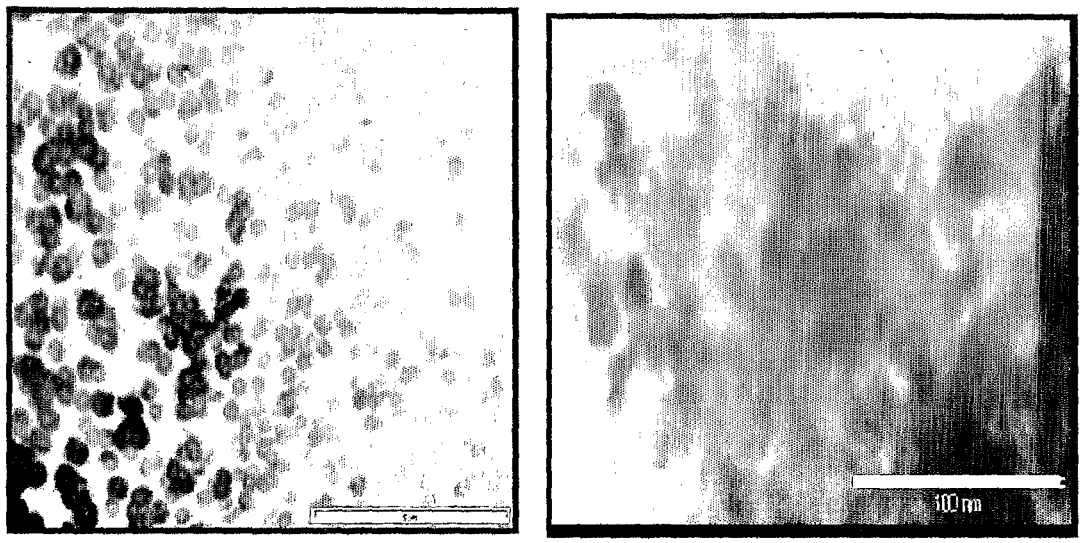

FIG. 7. Transmission Electron Microscopy (TEM) images of the nanostructured TiO2 reservoir synthesized at pH 3 (200,000×).

Figure 8:
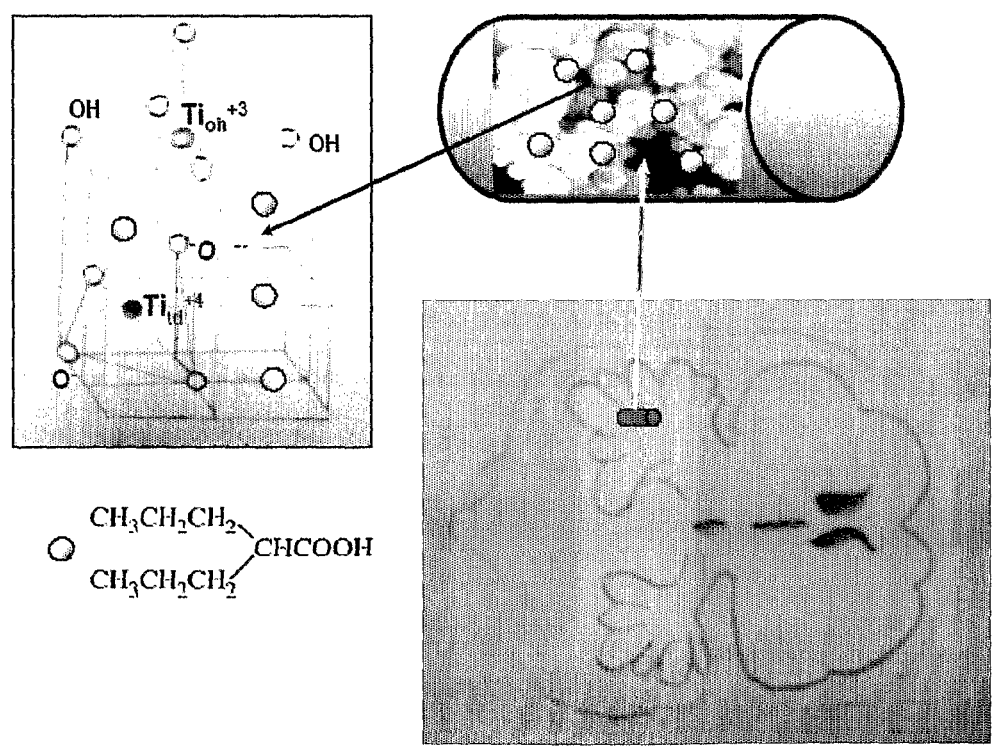

FIG. 8. Model of the reservoir and the drug release.

Figure 9:
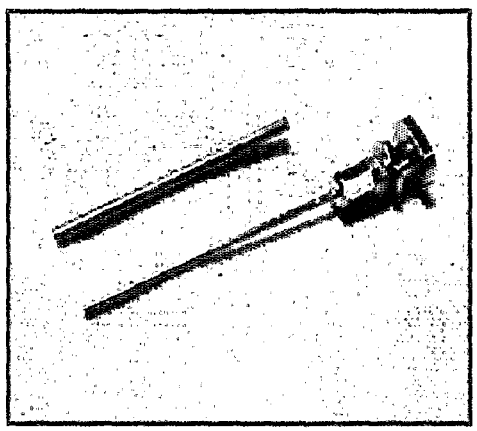
Figure 9:
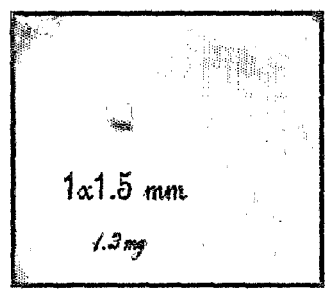
Figure 9:
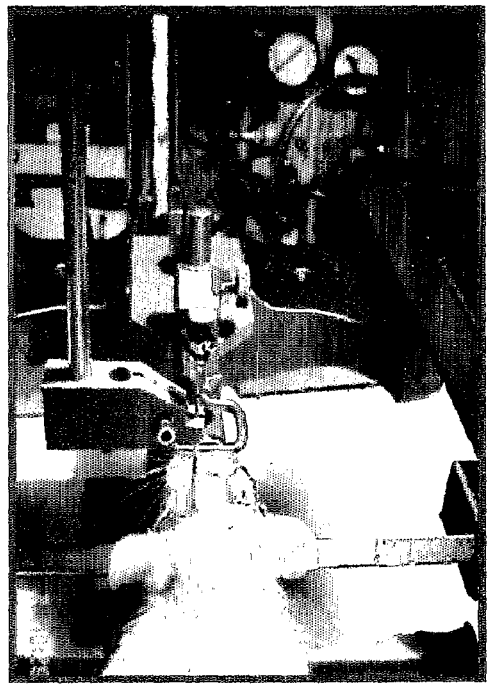

FIG. 9. This figure shows the technique used to implant a reservoir into the temporal lobe of the brain of a Winster rat. (a) The cannula that was used to obtain the cylinders used in the implant. (b) The biocompatible reservoir and the brain tissue show there is no damage to the tissue surrounding the implant. (c) Stereotactic surgery used to implant the reservoir.

Figure 10:
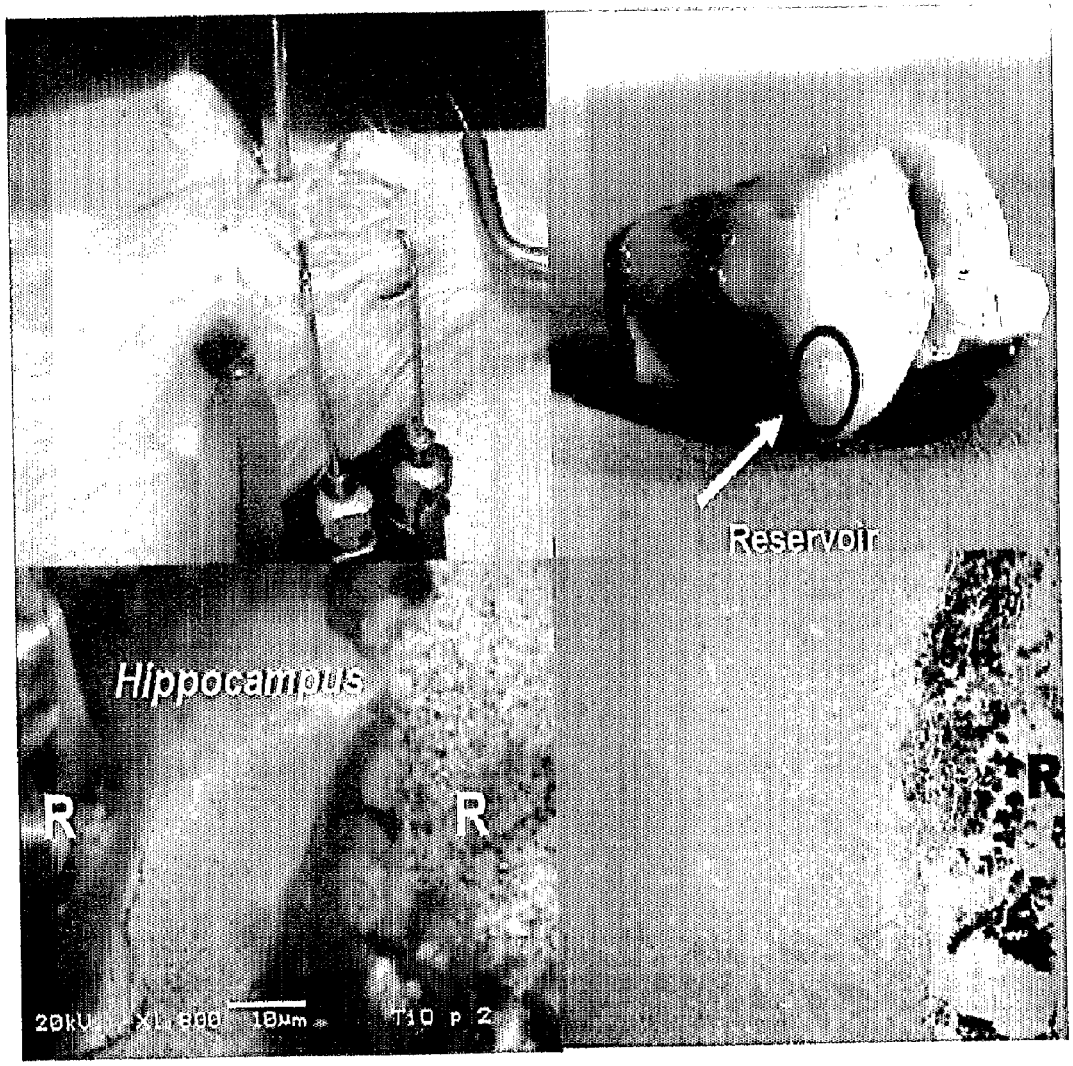

FIG. 10. The local effect of the ordered titania material implant was studied in the close vicinity of brain tissue. A well-organized fibrous capsule was formed surrounding the implant following an implantation period of 6 months or greater. The implant did not cause necrosis and inflammation was not observed. The histopathological study surrounding the implant was made. No pathology was reported. The results show that there was good biocompatibility with brain tissue.

Figure 11:
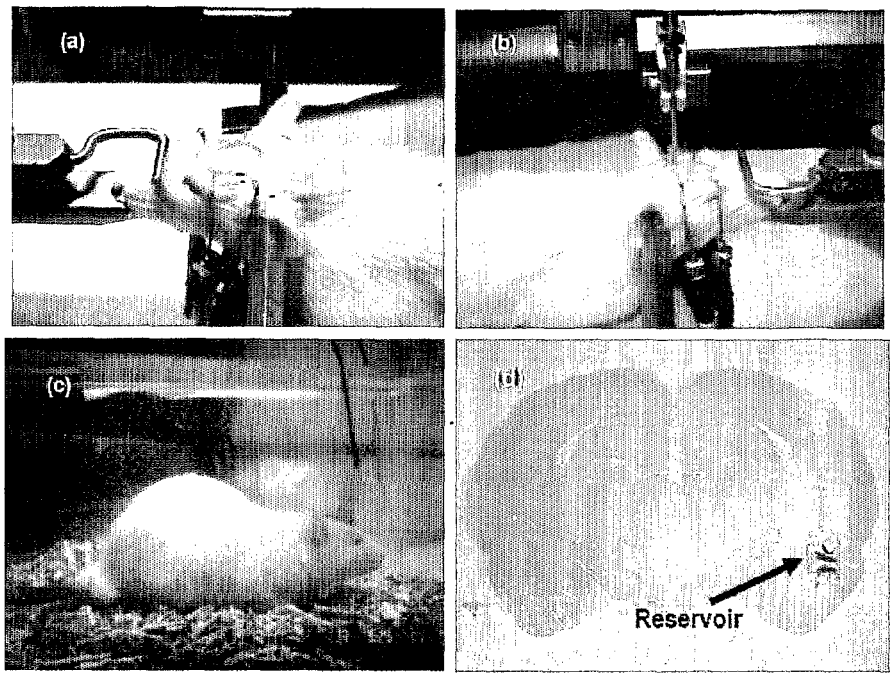

FIG. 11. Stereotactic surgery, rat conduct and histophatological study after one year.

Figure 12:
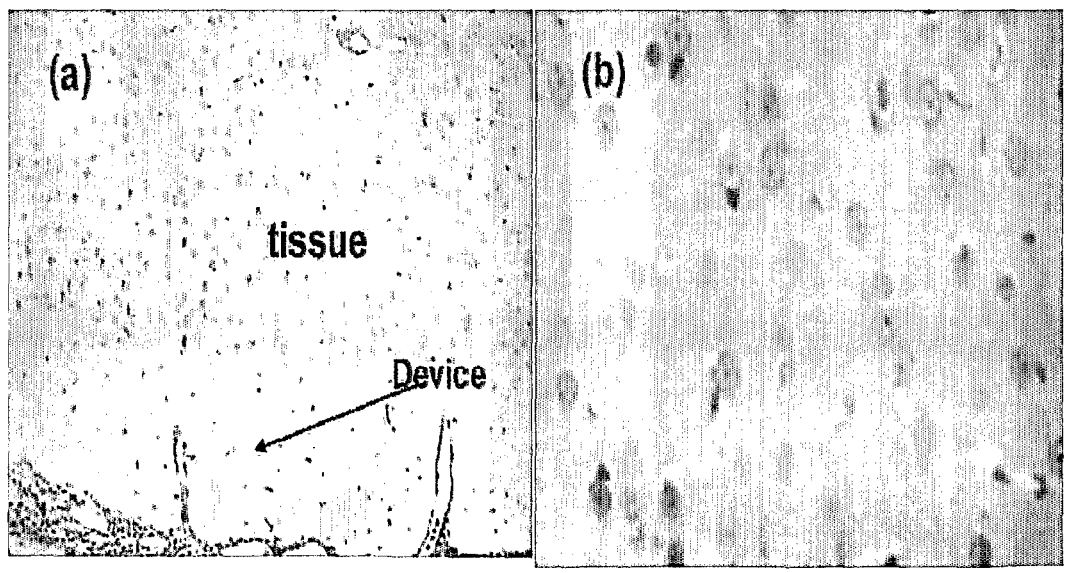

FIG. 12. The biocompatibility study of the brain was focussed on the chronic inflammatory response associated with the reservoir implantation procedure. This absence of alterations in implanted rats confirms a high degree of biocompatibility of the materials.

PURPOSE OF THE INVENTION

When taken orally, the absorption of a drug into the blood stream results in a considerable loss of the drug due to elimination through the urine and other organs in the body. As much as 86% is eliminated through the urine. In order to avoid this loss, implantation directly into an area adjacent to the affected region may result in considerable savings in the amount of the drug actually needed. Additionally, large fluctuations in the concentration of the drug can be avoided. In order for the controlled drug release to be effective several conditions need to be met as follows:

(1) The concentration of the drug released must be as constant as possible. Because the structure of the reservoir described in this invention is highly porous, diffusional processes through the porous structure of the reservoir are involved. The results obtained in this invention have shown that the rate of delivery is constant over periods of 6 months to three years. The rate of delivery is close to zero order in the concentration of the drug. In other words it is constant. Large fluctuations in the concentration of the drug during delivery are avoided.

(2) The implanted canister containing the drug must be biocompatible with the surrounding tissue. This biocompatibility is clearly shown in FIG. 11. Little, if any damage to the surrounding tissue was observed.

(3) The implantation process is reversible. When the concentration of the drug in the delivery process falls below that required for effective delivery the canister may be removed and reinserted with a fresh dose of the medication.

(4) In addition to the delivery of anticonvulsants, this device may be used in other applications, chemotherapy in the treatment of cancer for example.

(5) The nanoconstruction process using a sol-gel approach, results in a very small canister, which will decrease the damage induced in the implantation process.

(6) The mesoporous structure of the $TiO_2$ nanoreservoir permits microglial cells to access the interior of the implant.

The invention claimed is:

1. A sol-gel nanostructured titania reservoir in the form of a xerogel comprising silica, titania and silica-titania, obtained by the method comprising the steps of:
   i) putting in a three-necked flask a mixture consisting of 36 ml of deionized water; from 0 to 50 ml of ethylene diamine tetraacetic acid (EDTA) and 190 ml of tert-butanol;
   ii) adding $HNO_3$ to the solution in a dropwise manner in order to adjust the pH to 2 when a basic drug is to be occluded within the interior of the reservoir; and adding ammonium hydroxide in a dropwise manner to the solution to adjust the pH to 12 when an acidic drug is to be occluded within the interior of the reservoir; and refluxing the solution;
   iii) adding 87 ml of titanium n-butoxide and 21.5 ml of tetraethoxysilane to the solution being refluxed to obtain a colloidal suspension;
   iv) refluxing the colloidal suspension for an additional period of 24 hours;
   v) drying the samples under vacuum conditions at 104 mm Hg in order to remove excess water and alcohol; and
   vi) drying the samples at 30° C. for 72 hours using an inert atmosphere furnace, increasing the temperature at a rate of 0.25° C/min in order to reach the final drying temperature of 30° C.,
   wherein the pH is verified continually by means of a potentiometer during said refluxing;
   said reservoir having, if it comprises a drug, a constant rate of drug release over periods of 6 months to 3 years.

2. The sol-gel nanostructured titania reservoir of claim 1 that comprises partially hydrolyzed nano-materials having a Ti:Si range of compositions between (100:0 and 0:100).

3. A method of administering a controlled release central nervous system (CNS) drug to a patient in need thereof, wherein the drug is carried by the sol gel reservoir of claim 2.

4. A method for preparing the sol-gel nanostructured titania reservoir of claim 1, comprising the steps of:
   i) putting in a three-necked flask a mixture consisting of 36 ml of deionized water; from 0 to 50 ml of ethylene diamine tetraacetic acid (EDTA) and 190 ml of tert-butanol;
   ii) adding $HNO_3$ to the solution in a dropwise manner in order to adjust the pH to 2 when a basic drug is to be occluded within the interior of the reservoir; and adding ammonium hydroxide in a dropwise manner to the solution to adjust the pH to 12 when an acidic drug is to be occluded within the interior of the reservoir;
   and refluxing the solution;
   iii) adding 87 ml of titanium n-butoxide and 21.5 ml of tetraethoxysilane to the solution being refluxed to obtain a colloidal suspension;
   iv) refluxing the colloidal suspension for an additional period of 24 hours;
   v) drying the samples under vacuum conditions at 104 mm Hg in order to remove excess water and alcohol; and
   vi) drying the samples at 30° C. for 72 hours using an inert atmosphere furnace, increasing the temperature at a rate of 0.25° C/min in order to reach the final drying temperature of 30° C.,
   wherein the pH is verified continually by means of a potentiometer during said refluxing;

5. The sol-gel nanostructured titania reservoir of claim 1 which comprises a neurological drug occluded within its interior.

6. The sol-gel nanostructured titania reservoir of claim 1 which is biocompatible with a surrounding brain tissue.

7. The reservoir of claim 5 wherein the neurological drug is valproic acid.

* * * * *